(12) United States Patent
Harris

(10) Patent No.: US 7,112,221 B2
(45) Date of Patent: Sep. 26, 2006

(54) PROSTHESIS

(75) Inventor: David Harris, Shrewsbury (GB)

(73) Assignee: Finsbury (Development) Limited, Leatherhead (GB)

( * ) Notice: Subject to any disclaimer, the term of this patent is extended or adjusted under 35 U.S.C. 154(b) by 96 days.

(21) Appl. No.: 10/642,714

(22) Filed: Aug. 18, 2003

(65) Prior Publication Data

US 2004/0054409 A1 Mar. 18, 2004

(30) Foreign Application Priority Data

Aug. 19, 2002 (GB) .................................. 0219280.5

(51) Int. Cl.
*A61F 2/08* (2006.01)
(52) U.S. Cl. ...................... 623/13.11; 606/74; 606/151
(58) Field of Classification Search .... 623/13.11–13.2; 606/151, 228, 74; 24/16 R, 17 AP, 30.5 L
See application file for complete search history.

(56) References Cited

U.S. PATENT DOCUMENTS

| 3,469,573 | A | * | 9/1969 | Florio | ........................ | 606/74 |
| 3,577,837 | A | * | 5/1971 | Bader, Jr. | ................ | 623/13.15 |
| 5,601,604 | A | * | 2/1997 | Vincent | ...................... | 606/216 |
| 6,226,839 | B1 | * | 5/2001 | Sayegh | ..................... | 24/16 PB |

\* cited by examiner

*Primary Examiner*—Bruce Snow
(74) *Attorney, Agent, or Firm*—Senniger Powers

(57) ABSTRACT

A prosthetic implant is described for surgical implantation in a hand of a patient comprising an elongate flexible member (24; 32; 51) for passing snugly around a surgically exposed bone (21) of the hand, the elongate flexible member (24; 32; 51) having first and second end portions (25, 27; 35, 36; 54, 55) at opposite ends thereof, the first end portion (25; 35; 54) of the elongate flexible member (24; 32; 51) being provided with slot defining means (26; 34; 56) defining a slot for receipt of the second end portion (27; 36; 55) of the elongate flexible member (24; 32; 51), and locking means (-; -; 65) to secure the second end portion (27; 36; 55) to the first end portion (25; 35; 54) after insertion of the second end portion (27; 36; 55) in the slot.

29 Claims, 7 Drawing Sheets

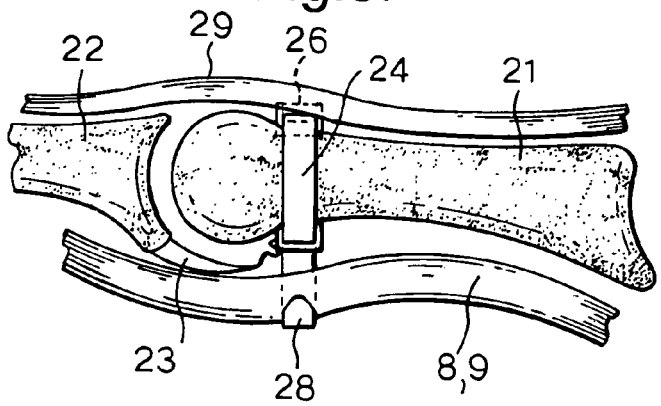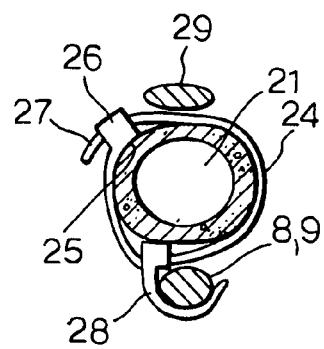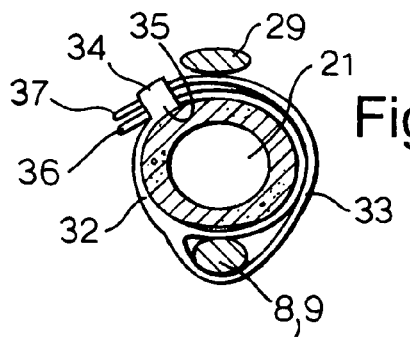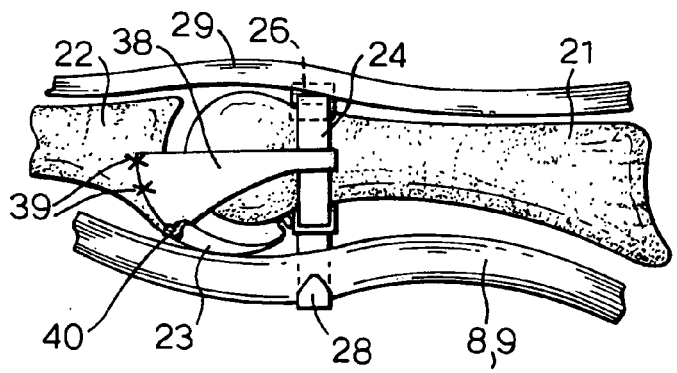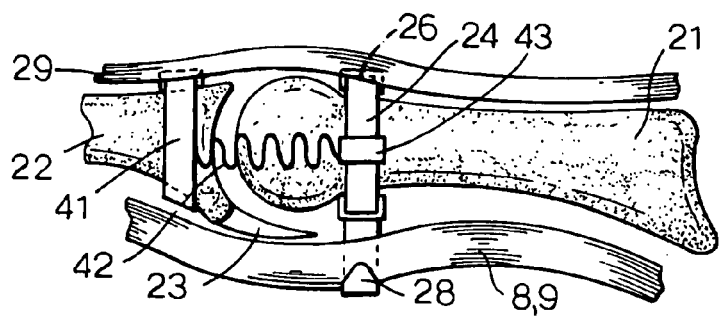

PROSTHESIS

This invention relates to a prosthesis, in particular a prosthesis to replace a flexor tendon pulley in the hand.

The fingers of the hand are moved by flexor and extensor tendons which extend from corresponding tensor and extensor muscles in the forearm. The extrinsic flexor tendons, of which there are two for each finger, are attached to the muscles flexor digitorum profundis and flexor digitorum superficialis respectively. At the level of the metacarpophalangeal joint, each superficialis tendon splits longitudinally into two parts. The two parts pass around the profundis tendon and then reunite before separating again to attach to either side of the palmar surfaces of the base of the middle phalanx. This peculiar arrangement of the superficialis tendon provides a tunnel which allows the profundis tendon to become superficial. The effect, so far as the superficialis tendon is concerned, is to increase the lever arm of the tendon at the proximal interphalangeal joint, thereby enabling a powerful grip of the fingers to be exerted. The tendon of the flexor digitorum profundis muscle eventually inserts into the bone of the palmar surfaces of the distal phalanx.

The tendons of the digital flexors are held in close proximity to the phalanges of each finger in each case by a fibrous sheath or retinaculum which acts to prevent so-called "bowstringing" of the tendons and ensure that their pull produces immediate movement at the interphalangeal joint. In addition fibro-osseous canals are formed by a shallow groove in the anterior surfaces of the phalanges and by a fibrous sheath which attaches to the raised lateral and medial edges of the proximal and middle phalanges and the palmar surface of the distal phalanx. Most of the fibres of this sheath are arranged transversely but at the interphalangeal joints they have a criss-cross arrangement to allow flexion to occur. In the region of the metacarpal phalangeal joint at the base of the fingers this strong criss-cross arrangement of fibres forms what is known as the palmar aponeurosis pulley.

Damage to this pulley can occur in several ways. For example, it can be cut, severed or crushed in an accident. The forces applied to the tendons in rock-climbing can rupture it. This produces displacement of the vector or line of action of the tendon on the finger, resulting in deformity of the finger and loss of normal movement and power of action.

Usually the pulley can be reconstructed with nearby tissues. This is, however, not always feasible or desirable.

Rheumatoid arthritis is a progressive, debilitating disease which mainly attacks the lining tissues of the joints and tendons. Swelling of these tissues causes stretching, weakening and destruction of the joints and tendons and their supporting tissues, including the palmar aponeurosis pulley and the ligaments of the joints. The resulting deformity and loss of use in the fingers is due to the combination of weakness of the support tissues and abnormal vector forces. The typical deformity produced is known as palmar subluxation of the metacarpophalangeal joint, often associated with ulnar drift of the fingers.

In these cases, reconstruction with the sufferer's own tissues is not satisfactory because they are likely to be weakened by the disease already or else they are likely to be weakened subsequently. The reconstructed result is therefore prone to deteriorate. A great deal of effort has been put into devising surgery to correct, or at least neutralise these deforming influences. So far there has been no long term solution, once the deformity becomes severe.

Therefore, there is a need in the art for a prosthetic implant for replacing damaged flexor tendon pulleys which are beyond surgical repair. Further, there is a need in the art for providing a prosthetic implant which is capable of combatting the abnormal forces experienced in the tendons of the hand and fingers and supporting ligaments as a result of the effects of rheumatoid arthritis.

According to the present invention there is provided a prosthetic implant for surgical implantation in a hand of a patient comprising an elongate flexible member for passing snugly around a surgically exposed bone of the hand, the elongate flexible member having first and second end portions at opposite ends thereof, the first end portion of the elongate flexible member being provided with slot defining means defining a slot for receipt of the second end portion of the elongate flexible member, and locking means to secure the second end portion to the first end portion after insertion of the second end portion in the slot.

A prosthetic implant according to the invention can be used as a simple pulley replacement. Alternatively, a prosthetic implant in accordance with the invention can be employed as a cerclage strap for the treatment of a fracture of the shaft of a metacarpal bone or phalanx.

The second end portion may be substantially rectangular in cross section while the slot defining means comprises a sleeve portion defining a substantially rectangular slot for receipt of the second end portion. Alternatively the second end portion can be substantially rectangular in cross section while the slot defining means comprises a sleeve portion defining an open topped slot for receipt of the second end portion. In a further variation of the prosthetic implant according to the invention the second end portion is substantially rectangular in cross section and the slot defining means comprises a sleeve portion defining a substantially C-section slot for receipt of the second end portion.

The slot may be an axis which is aligned substantially parallel to the axis of the first end portion. Alternatively the slot may have an axis which is aligned substantially perpendicular to the axis of the first end portion.

In a preferred form of prosthetic implant according to the invention the elongate flexible member has a bone-contacting surface which is adapted to contact a bone of a hand of a patient to which the prosthetic implant is to be secured and which is roughened to improve the gripping action of the elongate flexible member on the bone. Thus the bone-contacting surface of the flexible elongate member may be provided with spikes or ridges to relieve uniform pressure on the bone to which it is to be attached and to improve the grip of the elongate flexible member on the bone.

There may be further provided a flexor tendon support means adapted upon implantation thereof in a hand of a patient around a metacarpal bone thereof to pass under the ulnar side of the flexor tendons of the corresponding finger of the patient. Such a flexor tendon support means may comprise a hook-shaped appendage attached to the elongate flexible member and adapted for passing around the ulnar side of the flexor tendons of the finger, the hook-shaped appendage having an axis extending substantially in the plane of the axis of the flexible elongate member. Alternatively the flexor tendon support means may comprise a band attached at one end thereof to the elongate flexible member and adapted to pass on the ulnar side of the flexor tendons of the finger while the slot defining means further defines a second slot to receive a free end portion of the band at the opposite end from the one end thereof, the band having an axis which is substantially parallel to the axis of the elongate flexible member.

In a particularly preferred form of prosthetic implant the flexor tendon support means is integrally formed with the strap. In such a prosthetic implant the elongate flexible member may comprise a saddle shaped portion provided with a bearing surface adapted upon implantation of the prosthetic implant in the hand of a patient to underlie the flexor tendons of the finger on the ulnar side thereof, and first and second strap portions integrally formed with the saddle shaped portion and disposed so that the first strap portion extends from the saddle shaped portion on one side of the bearing surface and the second portion extends substantially in alignment with the first strap portion from the saddle shaped portion on the other side of the bearing surface. Such a saddle portion may have a relatively rigid central portion between more flexible end portions along the path of the flexor tendons.

Conveniently the slot defining means comprises a bridge portion integrally formed with the first strap portion and defining a substantially rectangular slot and the second strap portion is of substantially rectangular cross section and adapted for reception in the substantially rectangular slot.

Alternatively the slot defining means comprises a pair of cantilever portions defining with the first strap portion a substantially C-shaped section providing a slot for reception of the second strap portion and wherein the second strap portion is substantially of rectangular cross section and adapted for reception in the slot.

Ribs may be provided on each of the first and second strap portions adjacent the saddle shaped portion and adapted for contacting the patient's metacarpal bone so as to space the bearing surface therefrom and facilitate blood supply to the periosteum. Moreover the first strap portion can be provided on a side thereof corresponding to the bearing surface with a plurality of grooves which separate corresponding lands one from another.

The locking means may take different forms. For example, the locking means may comprise a series of teeth provided on the second strap portion and a corresponding series of teeth on the inside of the slot adapted to engage with the teeth on the second strap portion. Alternatively the locking means may comprise a plug adapted for passage through a bore made in overlapping ends of the first and second strap portions and extending substantially transversely into the patient's metacarpal bone. Such a plug preferably has a snap fit end for engagement in the bore in the patient's metacarpal bone.

It is envisaged that a prosthetic implant of the invention may be used in conjunction with a replacement metacarpophalangeal joint prosthesis (for example, a total metacarpal phalangeal joint replacement of the type disclosed in European Patent Publication No. 1203569). Such a prosthesis may already be in situ, or implanted at the same time. Hence the design of the prosthetic implant of the invention must be such as not to interfere with such a replacement metacarpophalangeal joint prosthesis, whether this is already implanted or is being implanted at the same time, or might be implanted at some future date.

It is further envisaged that a prosthetic implant of the invention may be linked to a replacement metacarpophalangeal joint prosthesis to work in conjunction therewith.

Also envisaged is a prosthetic implant wherein the elongate flexible member is adapted for passing snugly around a surgically exposed metacarpal bone of the hand and wherein the implant further includes a secondary member adapted for engagement with a corresponding phalangeal bone of the hand and flexibly connected to the elongate flexible member. The secondary member may comprise a further elongate flexible member adapted for passing snugly round the phalangeal bone, the further elongate flexible member having third and fourth end portions at opposite ends thereof, the third end portion of the further elongate flexible member being provided with second slot defining means defining a second slot for receipt of the fourth end portion of the further elongate flexible member, and second locking means to secure the fourth end portion to the third end portion after insertion of the fourth end portion in the slot. The elongate flexible member which is adapted for passing snugly around the surgically exposed metacarpal bone of the hand may be connected by spring means to the secondary member which is adapted for engagement with a corresponding phalangeal bone of the hand.

In a further preferred embodiment of the invention the elongate flexible member is adapted for passing snugly around a surgically exposed metacarpal bone of the hand and the implant further includes flexible attachment means flexibly connected to the elongate flexible member and adapted for securement to a corresponding phalangeal bone of the hand. In such an embodiment the flexible attachment means can be adapted for securement to the phalangeal bone by means of pins, staples, or adhesive.

The invention also contemplates a prosthetic implant which can be used in conjunction with a total metacarpal phalangeal joint replacement, for example, a total metacarpal phalangeal joint replacement of the type illustrated in European Patent Publication No. 1203569. In such a prosthetic implant the elongate flexible member can be adapted for passing snugly around a surgically exposed metacarpal bone of the hand and be provided with a lateral hook-shaped member whose free end is adapted for insertion in a surgically prepared cavity in the metacarpal bone intended for receipt of a metacarpal part of a total metacarpal phalangeal joint replacement.

The invention further contemplates a sterilised package containing a prosthetic implant as described above. Such a package may comprise, for example, a sealed plastics bag containing the prosthetic implant which can be sterilised in any known manner, for example exposure to radiation, heat sterilisation, exposure to ethylene oxide, and the like. A variety of sterilisation techniques may be used.

In order that the invention may be clearly understood and readily carried into effect, some preferred embodiments thereof will now be described, by way of example only, with reference to the accompanying diagrammatic drawings, wherein:

FIG. 3 is a side view of a metacarpophalangeal joint fitted with a prosthetic implant in accordance with the invention;

FIG. 4 is a cross section through the metacarpal bone of FIG. 3;

FIG. 5 is a cross section through a metacarpal bone fitted with a second form of prosthetic implant in accordance with the invention;

FIG. 6 is a side view of a third form of prosthetic implant in accordance with the invention implanted at a metacarpophalangeal joint;

FIG. 7 is a fourth form of prosthetic implant in accordance with the invention implanted at a metacarpophalangeal joint;

Figure 1A:
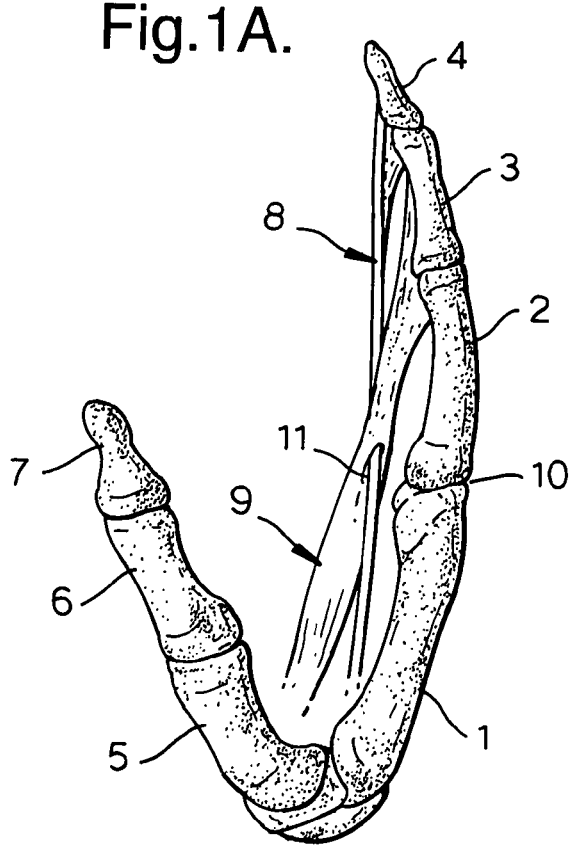
FIG. 1A is a diagrammatic side view of the bones of a human right hand and of the flexor tendons associated with the index finger thereof.

Referring to the drawings, and to FIG. 1A in particular, a human right hand includes a metacarpal bone 1, and an index finger with a proximal phalanx 2, a middle phalanx 3, and a distal phalanx 4, while its thumb comprises a metacarpal bone 5, a proximal phalanx 6, and a distal phalanx 7. Movement of the index finger is caused by the flexor digitorum profundus muscle of the forearm which is connected to its corresponding tendon 8 and by the flexor digitorum superficialis muscle also located in the forearm which operates its corresponding tendon 9. In the vicinity of the metacarpophalangeal joint 10 the tendon 9 of flexor digitorum superficialis splits longitudinally in two halves and then rejoins again to provide a tunnel 11 for the tendon 8 of flexor digitorum profundus.

Figure 1B:
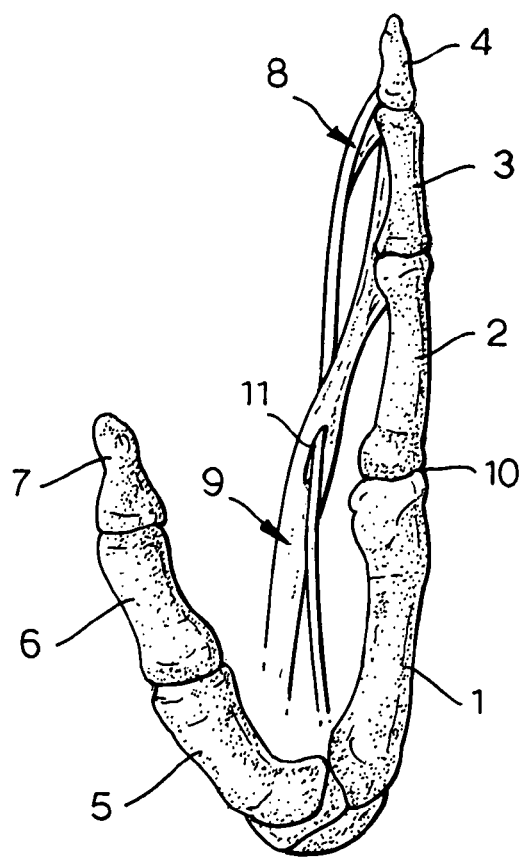
FIG. 1B is a diagrammatic side view of the bones of a human right hand with a straightened finger.
Figure 1C:
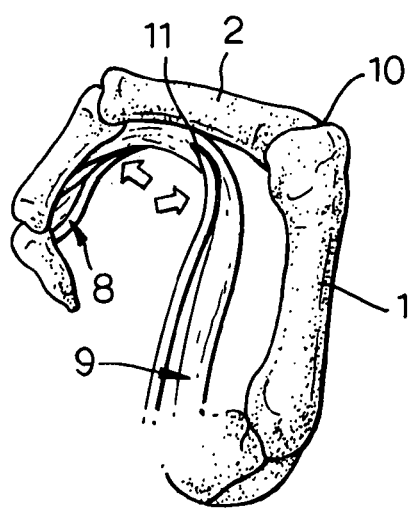
FIG. 1C is a diagrammatic side view of the bones of a human right hand with a bent finger.

Comparison of FIGS. 1B and 1C illustrates the need for the A1 and A2 pulleys, in particular, to retain the flexor tendons during flexion of the finger so that they can follow the curvature of the bent finger.

Figure 2:
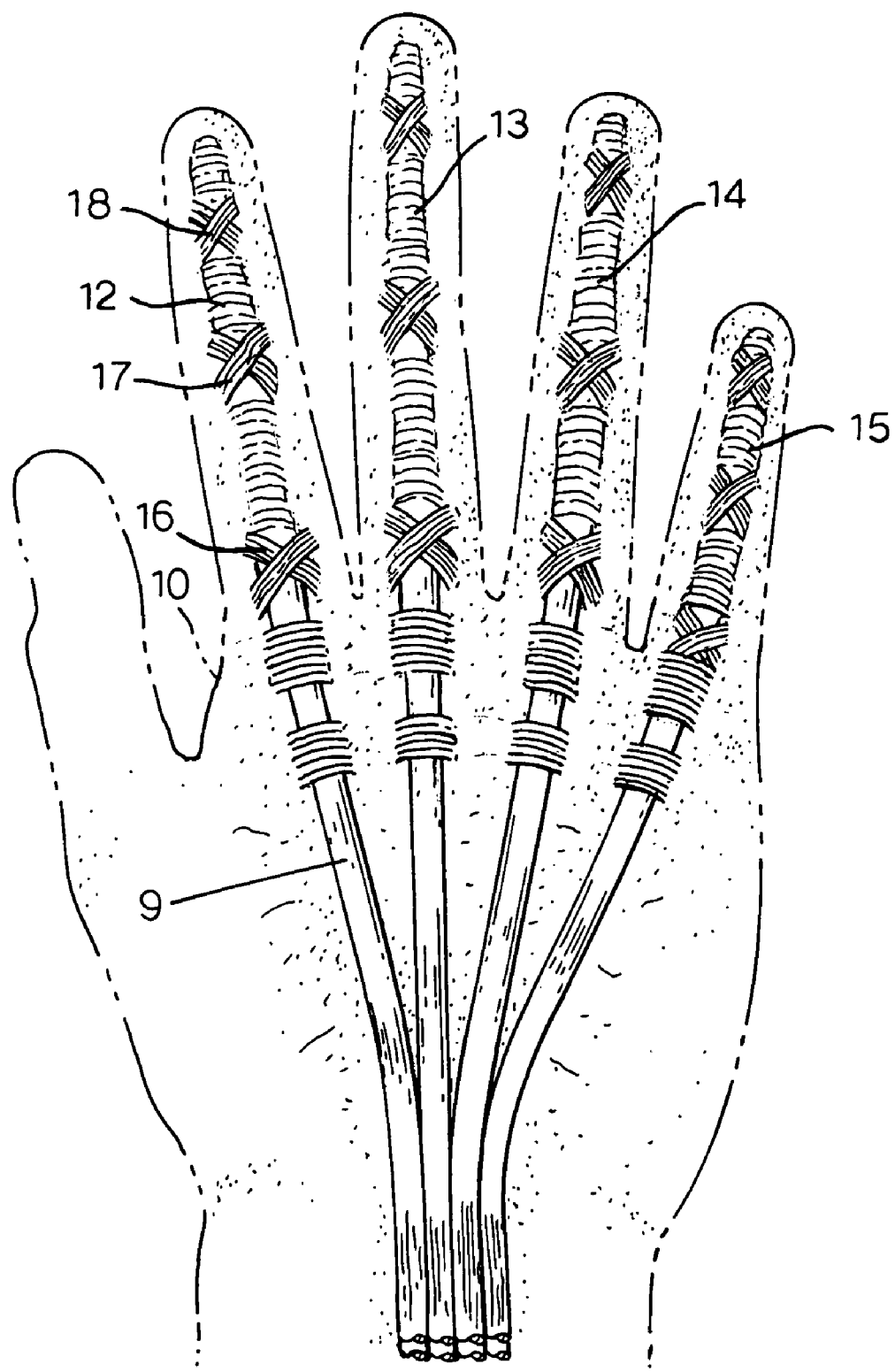
FIG. 2 is a diagrammatic view of the palmar fascia of the hand.

FIG. 2 shows the palmar fascia of a left hand. This shows fibrous flexor sheaths 12, 13, 14, 15 for each of the fingers of the hand, while the fibro-osseous canals of the index finger are indicated by reference numerals 16, 17 and 18. The criss-cross nature of the osseous canals 16, 17 and 18 can be seen in FIG. 2.

FIG. 3 shows a metacarpal bone 21 and a phalanx 22, with a palmar plate 23. A prosthesis comprising a flexible strap 24 made of a biocompatible polymer, such as polyethylene, polypropylene, or nylon, has been applied around the neck of the surgically exposed metacarpal bone 21. At a first end of strap 24 there is a buckle device 26. This can, for example, comprise a box-section portion with an orifice extending in the plane of the axis of the strap 24 and substantially parallel to the portion of that axis which is defined by an immediately adjacent first end portion of strap 24. On the inner side of that orifice which is the closer to the metacarpal bone 21 when the strap 24 is applied to the metacarpal bone there is provided a series of teeth which are adapted to engage with corresponding teeth on a second end portion 27 of strap 24 at the other end of the strap 24. The second end portion 27 of the strap 24 is designed to be a snug fit in the orifice so that, upon inserting that second end portion 27 through the orifice and pulling the strap 24 tight, the teeth on the second end portion engage with the teeth on the inside of the orifice and lock the strap 24 firmly to the metacarpal bone 21.

In order to assist in anchoring the strap 24 to the metacarpal bone 21 and to prevent it from rotating about the axis of metacarpal bone 21 after implantation, the inner surface of the strap 24 is roughened by being provided with spikes or ridges. The provision of such a roughened surface on the inner face of strap 24 further permits soft tissue capture or ingrowth, thus encouraging development of a natural fibrous envelope strengthening the implant and protecting the tissues moving over it. In addition it relieves uniform pressure on the metacarpal bone 21.

To complete the prosthesis of FIGS. 3 and 4 strap 24 carries a secondary structure 28 which is hook-shaped in cross section and closed on the ulnar side of the flexor tendons 8, 9. The purpose of the hook 28 of prosthetic implant 24 of FIGS. 3 and 4 is to restore the lie of the flexor tendons 8, 9 to a position close to the exterior surface of the metacarpal bone 21, so that these lie approximately parallel to the axis of the metacarpal bone 21, and to prevent abnormal movement of the flexor tendons 8, 9, both in a planar direction, which is known as bowstringing, and also in an ulnar direction during flexor muscle action as part of the abnormal force vectors causing ulnar drift.

In the course of applying the strap 24 to the surgically exposed metacarpal bone 21 the surgeon passes the strap 24 around the metacarpal bone 21 behind, i.e. dorsal to, the flexor tendons 8, 9 and to palmar plate 23, as well as behind the extensor tendon 29. He then threads the second end portion 27 of the strap 24 through the orifice in the box-section portion 26 and pulls on the free end of the second end portion 27 to tighten the strap 24 until it fits snugly around metacarpal bone 21 without any tendency to rotate about the axis of metacarpal bone 21. As a result of interengagement of the teeth on the second end portion 27 with the teeth of the box-section portion 26, the strap 24 is held securely in place when the surgeon releases his grip on the free end of the strap 24. The free end portion of the strap 24 protruding from the box-section portion 26 can then be trimmed off prior to the surgical wound being closed up.

Instead of the axis of the orifice in the box-section portion 26 being substantially parallel to the axis of the adjacent first end portion it can alternatively be arranged to be substantially perpendicular to the axis of the adjacent portion of strap 24. In another variant the box-section portion 26 can be replaced by an open topped channel in which the second end portion 27 is a jam fit; in this case the teeth can be provided in the side walls of the channel with corresponding teeth being provided on the sides of the second end portion 27 of strap 24.

In FIG. 5 there is illustrated a second design of prosthesis in accordance with the invention which comprises a strap 32 with a much longer attachment 32 than the hook 27 of the embodiment of FIGS. 3 and 4 which extends all the way around flexor tendons 8, 9. A buckle device 34 at one end 35 of strap 31 has two box-section orifices aligned substantially parallel with the axis of the strap 24, one being for reception of a second end portion 36 of strap 31 and the other accommodates a second end portion 37 of attachment 33. The interior of each box-section orifice is provided with teeth for engagement with corresponding teeth on the corresponding free end 36 or 37 for locking that free end in the buckle device 34.

In addition to or as an alternative to using interlocking of teeth to lock free end 27 of strap 24 in place in buckle 26, it is also possible to use an adhesive to secure the free end 27 to the buckle device 26. Similarly an adhesive can be used to lock free ends 36 and/or 37 in place in buckle 34.

Although straps 24 and 32 have been described as being made of a plastics material they can alternatively be made of a biocompatible metal such as titanium. In this case a screw clamp arrangement can be used as a buckle device to lock one end of the strap 24 or 32 to the other in place around the neck of the metacarpal bone 21.

FIG. 6 illustrates a third form of prosthetic implant according to the invention. The same reference numerals have been used in FIG. 6 as in the earlier Figures to indicate like items. This embodiment includes a flexible attachment 38 which has a loop at its proximal end through which strap 24 can be passed before it is tightened up on the patient's metacarpal bone by the surgeon. At its distal end attachment 38 is secured by pins or staples 39 to phalanx 22. A further pin or staple 40 can be used, if desired, to secure attachment 38 also to palmar plate 23.

Instead of using pins or staples 39 and/or 40, a suitable adhesive, such as a cyanoacrylate adhesive (or superglue) could be used to secure attachment 38 to phalanx 22 or to palmar plate 23. Any suitable flexible material can be used for making attachment 38, for example a very fine polypropylene mesh or a non-woven material.

A fourth form of prosthetic implant is shown in FIG. 7. Again, like reference numerals have been used to indicate similar items to those indicated in previous Figures. In this embodiment a further strap 41 is secured by the surgeon around the patient's phalanx 22. This is connected by means of a spring 42 which has at its proximal end a loop 43 through which strap 24 is passed before it is tightened around the patient's metacarpal bone 21 by the surgeon.

The purpose of attachment 38, and also of strap 41 and spring 42, is to overcome the ulnar angulation of the finger which has been lost as a result of incompetence of the radial collateral ligaments.

Figure 8:
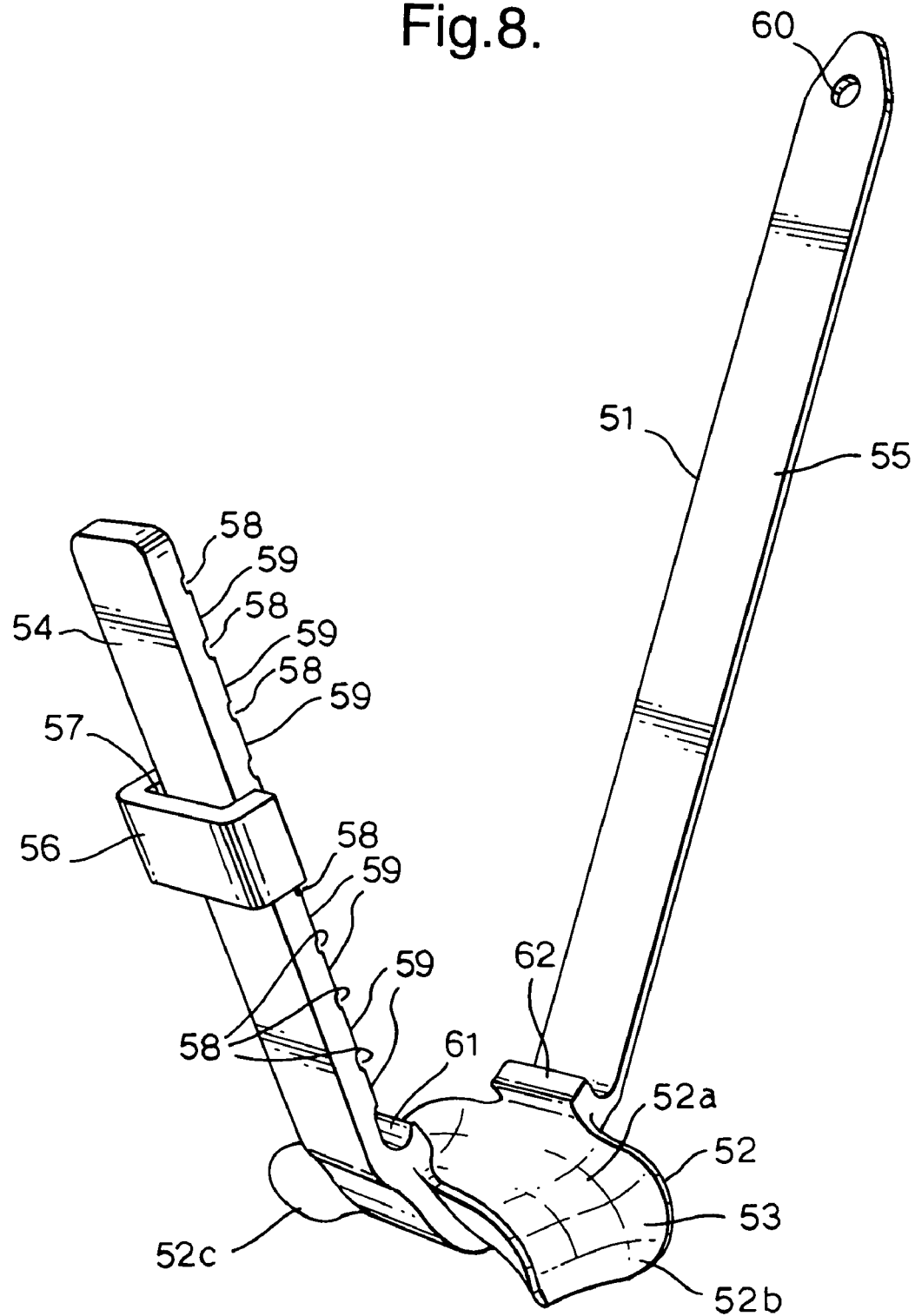
FIG. 8 is a perspective view of a fifth embodiment of the invention on an enlarged scale.
Figure 9:
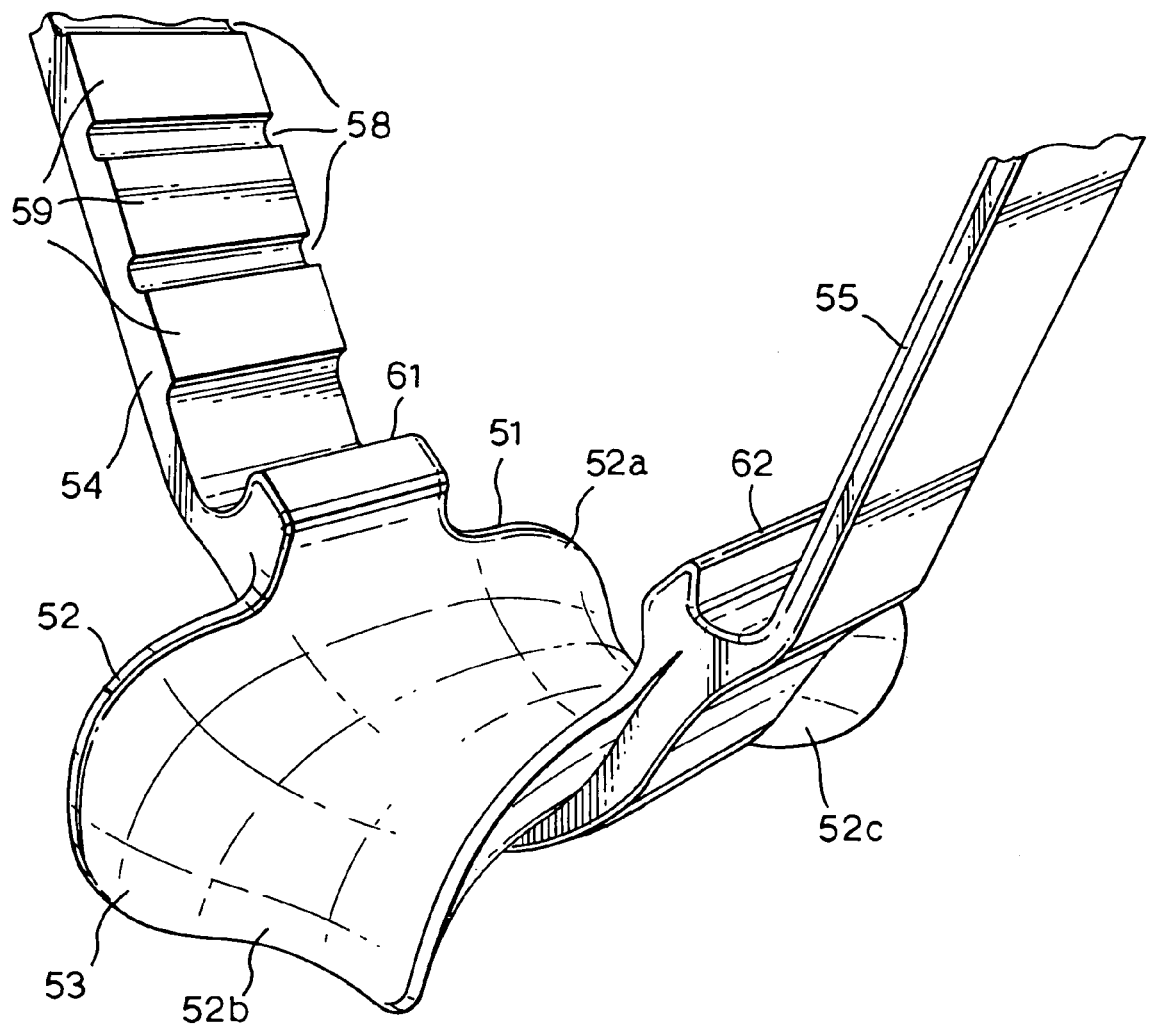
FIG. 9 is a view of part of the prosthesis of FIG. 8 on a still larger scale.

FIGS. 8 and 9 illustrate a fifth form of prosthesis 51 according to the invention. This is integrally moulded in one piece from polyethylene, polypropylene, nylon, or other suitable biocompatible plastics material. Prosthesis 51 comprises a contoured saddle portion 52 whose upper surface 53 (as illustrated) is intended to provide a bearing surface for the flexor tendon of the finger at whose metacarpophalangeal joint the prosthesis 51 is to be implanted. Saddle portion 52 includes a relatively rigid central portion 52a but it reduces in thickness towards lips 52b and 52c along the path of the flexor tendons so that the end portions adjacent lips 53b and 53c are more flexible than central portion 53a.

From one side of saddle portion 52 there extends upwardly at an angle (as illustrated in FIG. 8) a first strap portion 54, while a second strap portion 55 extends upwardly from saddle portion 52 on the opposite side of surface 53 so as to from a generally V-shaped prosthesis. A bridge portion 56 is provided on first strap portion 54 which defines therewith a generally rectangular section slot 57 for receipt of a free end portion of second strap portion 55 after the prosthesis 51 has been wrapped by the surgeon around the patient's surgically exposed metacarpophalangeal bone. In addition the inner face of first strap portion 54 is provided with a series of transverse grooves 58 which provide separation between a series of lands 59. At its free end second strap portion 55 is provided with a hole 60 through which a suture may be passed for a purpose which be described hereafter. At the junction between saddle portion 52 and first strap portion 54 there is a rib 61. There is a corresponding rib 62 at the junction between second strap portion 55 and saddle portion 52.

Figure 10:
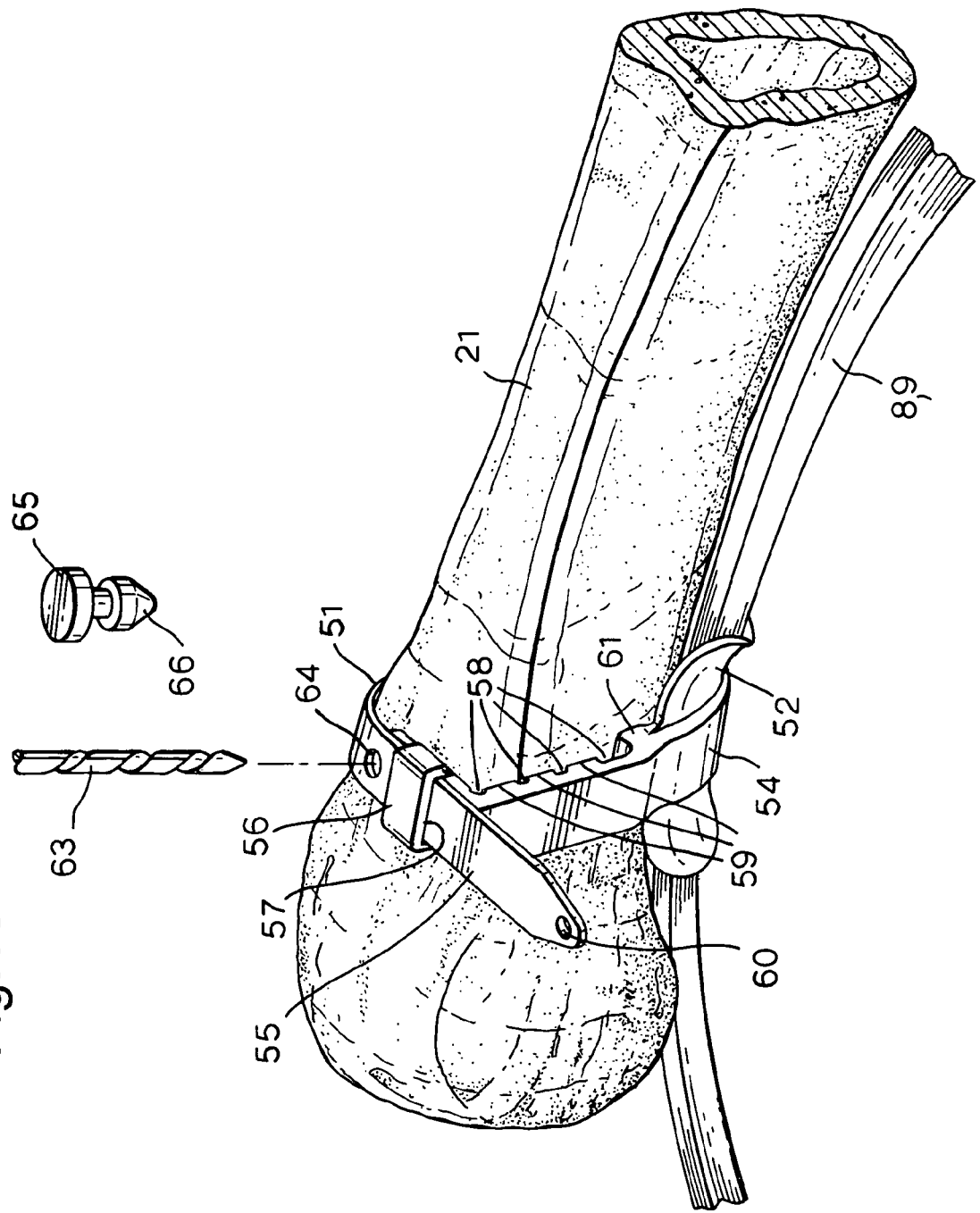
FIG. 10 is a diagrammatic view of a metacarpal bone to which the prosthesis of FIGS. 8 and 9 is being applied.

In FIG. 10 the phalanx of the patient is not shown for the sake of simplicity. It will be appreciated that this Figure illustrates the situation after the surgeon has threaded the prosthesis 51 around the distal end of the patient's metacarpophalangeal bone 21, with the saddle portion 52 positioned so that its bearing surface 53 is in contact with the flexor tendon 8 or 9 and provides a running surface against which these can slide to move the patient's fingers after completion of the surgical operation and a suitable period of recuperation.

To thread the prosthesis around the patient's metacarpal bone 21 the surgeon can use a curved needle to draw a suture tied at its other end through hole 60 along the desired path to be followed by the prosthesis 51, followed by the prosthesis 51, despite the limited access to the site of its implantation.

Ribs 61, 62 bear against the metacarpal bone 21 and ensure that the correct spacing between the bearing surface 53 and the metacarpal bone 21 is maintained so as to facilitate blood supply to the periosteum. (In FIG. 10 only rib 61 is visible). The free end of second strap portion 55 has also been inserted through slot 57 formed by bridge portion 56 and first strap portion 54. A suture can be tied through hole 60 to facilitate this step. It can then be tightened by use of a suitable tightening device (not shown) or by pulling on the suture engaged in hole 60. While maintaining the resulting tension in the second strap portion 55, the surgeon uses a drill (not shown) whose bit 63 is used to make a bore 64 through the overlapping ends of the second strap portion 55 and the first strap portion 51 and transversely into the patient's metacarpal bone 21. Without disturbing the alignment of the bore thus drilled, a plug 65 with a pointed snap fit end 66 is then inserted into the bone so that the pointed end 66 of plug 65 is received within, and retained by, the bore in the patient's metacarpal bone 21. Not only does plug 65 maintain the requisite amount of tension in the prosthetic implant 51 but also it anchors it to the metacarpal bone 21 and prevents accidental rotational movement of the prosthetic implant 51 around the axis of metacarpal bone 21. After anchoring the prosthetic implant 51 in this way the surgeon can then cut off the free end of second strap portion 56 adjacent from where it emerges from slot 57 before closing up the surgical wound and suturing it.

If desired plug 65 can be integrally formed with the second strap portion 55.

Figure 11:
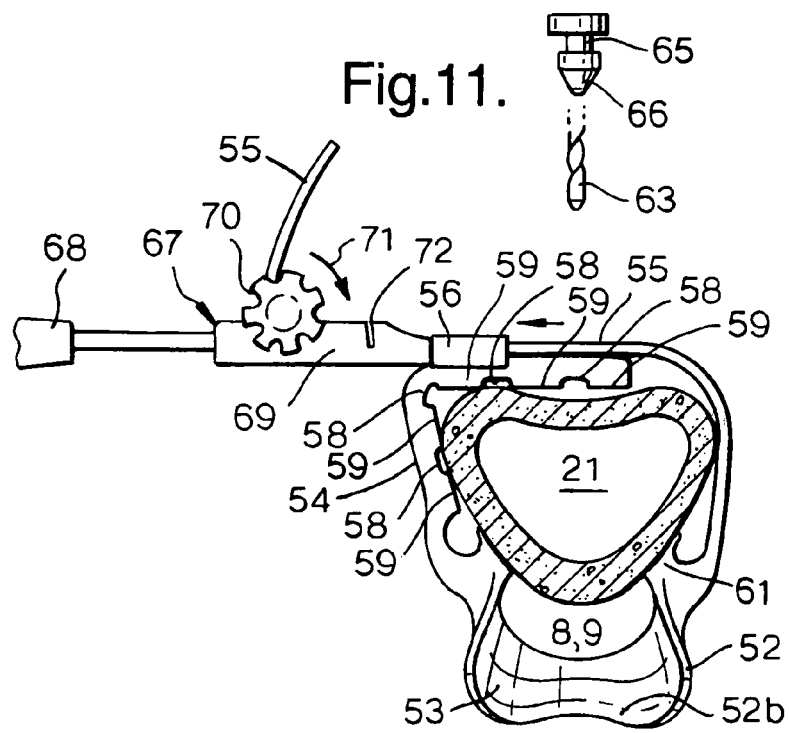
FIG. 11 is a cross section through a metacarpal bone and illustrates a tool for tightening the prosthesis of FIGS. 8 to 10 on the metacarpal bone.

In FIG. 11 there is illustrated diagrammatically a simple tensioning tool 67. This has a handle 68, only part of which is shown in FIG. 11 at its distal end and a hollow block 59 at its proximal end which has a rectangular section orifice in it whose axis extends substantially in the plane of the finger for receipt of the free end of strap portion 55. Reference numeral 70 indicates an operating knob which is mounted on an axle (not shown) that bears tightly against the free end of strap portion 55 so that, when operating knob 70 is rotated as indicated by arrow 71 it draws the end of second strap portion 55 into block 69 to tighten the prosthesis 51 on the metacarpal bone 21, while simultaneously drawing block 69 against bridge portion 56. The sharply curved pathway which the free end of strap portion 55 is caused to follow ensures that the axle of operating knob 70 exerts a tight grip on strap portion 55 without risk of slippage and inadvertent release of tension in the prosthetic implant 51 during the tightening operation. When the surgeon is satisfied that the correct tension has been achieved, he can use the drill with its drill bit 63 to form a bore 64 through strap portions 55 and 54 into metacarpal bone 21 for insertion of plug 65.

A slot 72 is provided in block 69 to accommodate a scalpel or other cutting instrument to chop off the unwanted free end of strap portion 55. The surgical wound can then be closed up in conventional manner.

The grooves 58 not only provide interruptions between the lands 59 so that uniform pressure is not applied to the entire periphery of the metacarpal bone 21 but also they facilitate flexing of the first strap portion 54 so that this can more readily curve to follow the contour of the metacarpal bone 21.

Figure 12:
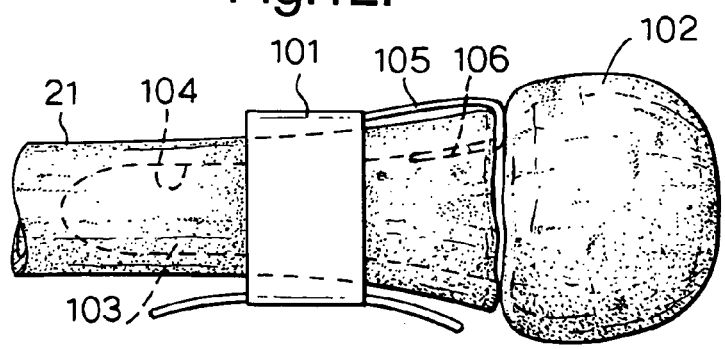
FIG. 12 is a diagrammatic side view of a further embodiment of the invention.
Figure 13:
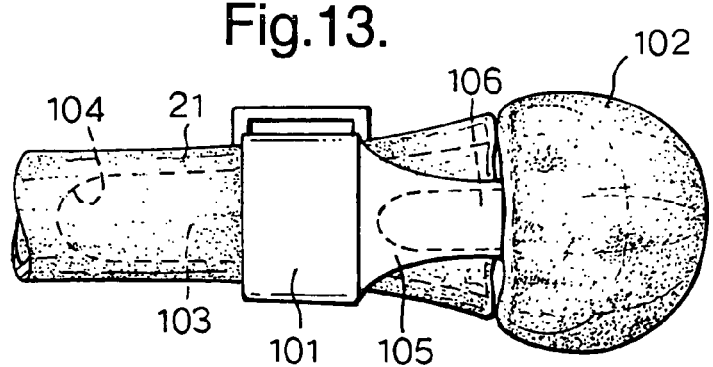
FIG. 13 is a diagrammatic dorsal view of the prosthetic implant of FIG. 12.

In the prosthetic implant of FIGS. 12 and 13 there is shown a prosthetic implant 101 which is designed for use in conjunction with a total metacarpal phalangeal joint replacement of the type disclosed in European Patent Publication No. 1203569. Such a total metacarpal phalangeal joint replacement includes a metacarpal insert member 102 which is received in a metacarpal plug member 103 fitted within a surgically prepared cavity 104 in the metacarpal bone 21 of a patient's hand. For further details of such a total metacarpal phalangeal joint replacement the attention of the reader is directed to European Patent Publication No. 1023569.

Prosthetic implant 101 is generally similar to implant 51 with the exception that it is provided with an integral lateral hook-shaped extension 105 whose free end 106 is adapted for insertion in the surgically prepared cavity 104.

The invention claimed is:

1. A prosthetic implant for surgical implantation in a hand of a patient to replace a flexor tendon pulley, said prosthetic implant comprising an elongate flexible member for passing snugly around a surgically exposed bone of the hand, the elongate flexible member having first and second end portions at opposite ends thereof, the first end portion of the elongate flexible member being provided with a slot defining means defining a slot for receipt of the second end portion of the elongate flexible member, and locking means to secure the second end portion to the first end portion after insertion of the second end portion in the slot, said prosthetic implant further comprising a flexor tendon support means adapted upon implantation thereof in a hand of a patient around a metacarpal bone thereof to pass under the ulnar side of the flexor tendons of the corresponding finger of the patient, the support being shaped to hold the flexor tendons to the metacarpal bone while limiting compression of the flexor tendons against the metacarpal bone.

2. A prosthetic implant according to claim 1, wherein the second end portion is substantially rectangular in cross section and wherein the slot defining means comprises a sleeve portion defining a substantially rectangular slot for receipt of the second end portion.

3. A prosthetic implant according to claim 1, wherein the slot has an axis which is aligned substantially parallel to the axis of the first end portion.

4. A prosthetic implant according to claim 1, wherein the elongate flexible member has a bone-contacting surface which is adapted to contact a bone of a hand of a patient to which the prosthetic implant is to be secured and which is roughened to improve the gripping action of the elongate flexible member on the bone.

5. A prosthetic implant according to claim 4, wherein the bone-contacting surface of the flexible elongate member is provided with ridges to relieve uniform pressure on the bone to which it is to be attached and to improve the grip of the elongate flexible member on the bone.

6. A prosthetic implant according to claim 1, wherein the flexor tendon support means comprises a hook-shaped appendage attached to the elongate flexible member and adapted for passing around the ulnar side of the flexor tendons of the finger, the hook-shaped appendage having an axis extending substantially in the plane of the axis of the flexible elongate member.

7. A prosthetic implant according to claim 1, wherein the flexor tendon support means comprises a band attached at one end thereof to the elongate flexible member and adapted to pass on the ulnar side of the flexor tendons of the finger and wherein the slot defining means further defines a second slot to receive a free end portion of the band at the opposite end from the one end thereof, the band having an axis which is substantially parallel to the axis of the elongate flexible member.

8. A prosthetic implant according to claim 1, wherein the flexor tendon support means is integrally formed with the strap.

9. A prosthetic implant according to claim 1, wherein the locking means comprises a plug adapted for passage through a bore made in overlapping ends of the first and second strap portions and extending substantially transversely into the patient's metacarpal bone.

10. A prosthetic implant according to claim 9, wherein the plug has a snap fit end for engagement in the bore in the patient's metacarpal bone.

11. A prosthetic implant according to claim 1, wherein the elongate flexible member is adapted for passing snugly around a surgically exposed metacarpal bone of the hand and wherein the implant further includes a secondary member adapted for engagement with a corresponding phalangeal bone of the hand and flexibly connected to the elongate flexible member.

12. A prosthetic implant according to claim 11, wherein the secondary member comprises a further elongate flexible member adapted for passing snugly round the phalangeal bone, the further elongate flexible member having third and fourth end portions at opposite ends thereof, the third end portion of the further elongate flexible member being provided with second slot defining means defining a second slot for receipt of the fourth end portion of the further elongate flexible member, and second locking means to secure the fourth end portion to the third end portion after insertion of the fourth end portion in the slot.

13. A prosthetic implant according to claim 12, wherein the elongate flexible member which is adapted for passing snugly around the surgically exposed metacarpal bone of the hand and is connected by spring means to the secondary member which is adapted for engagement with a corresponding phalangeal bone of the hand.

14. A prosthetic implant according to claim 1, wherein the elongate flexible member is adapted for passing snugly around a surgically exposed metacarpal bone of the hand and wherein the implant further includes flexible attachment means flexibly connected to the elongate flexible member and adapted for securement to a corresponding phalangeal bone of the hand.

15. A prosthetic implant according to claim 14, wherein the flexible attachment means is adapted for securement to the phalangeal bone by means of pins, staples, or adhesive.

16. A prosthetic implant according to claim 1, wherein the elongate flexible member is adapted for passing snugly around a surgically exposed metacarpal bone of the hand and is provided with a lateral hook-shaped member whose free end is adapted for insertion in a surgically prepared cavity in the metacarpal bone intended for receipt of a metacarpal part of a total metacarpal phalangeal joint replacement.

17. A sterilised package containing a prosthetic implant according to claim 1.

18. A prosthetic implant for surgical implantation in a hand of a patient to replace a flexor tendon pulley, said prosthetic implant comprising an elongate flexible member for passing snugly around a surgically exposed bone of the hand, the elongate flexible member having first and second end portions at opposite ends thereof, the first end portion of the elongate flexible member being provided with a slot defining means defining a slot for receipt of the second end portion of the elongate flexible member, and locking means to secure the second end portion to the first end portion after insertion of the second end portion in the slot, wherein the elongate flexible member comprises a saddle shaped portion provided with a bearing surface adapted upon implantation of the prosthetic implant in the hand of a patient to underlie the flexor tendons of the finger on the ulnar side thereof, and first and second strap portions integrally formed with the saddle shaped portion and disposed so that the first strap portion extends from the saddle shaped portion on one side of the bearing surface and the second portion extends substantially in alignment with the first strap portion from the saddle shaped portion on the other side of the bearing surface.

19. A prosthetic implant according to claim 18, wherein the second end portion is substantially rectangular in cross section and wherein the slot defining means comprises a sleeve portion defining a substantially rectangular slot for receipt of the second end portion.

20. A prosthetic implant according to claim 18, wherein the slot has an axis which is aligned substantially parallel to the axis of the first end portion.

21. A prosthetic implant according to claim 18, wherein the elongate flexible member has a bone-contacting surface which is adapted to contact a bone of a hand of a patient to which the prosthetic implant is to be secured and which is roughened to improve the gripping action of the elongate flexible member on the bone.

22. A prosthetic implant according to claim 21, wherein the bone-contacting surface of the flexible elongate member is provided with ridges to relieve uniform pressure on the bone to which it is to be attached and to improve the grip of the elongate flexible member on the bone.

23. A prosthetic implant according to claim 18, wherein the slot defining means comprises a bridge portion integrally formed with the first strap portion and defining a substantially rectangular slot and wherein the second strap portion is of substantially rectangular cross section and adapted for reception in the substantially rectangular slot.

24. A prosthetic implant according to claim 18, wherein ribs are provided on each of the first and second strap portions adjacent the saddle shaped portion and adapted for contacting the patient's metacarpal bone so as to space the bearing surface therefrom and facilitate blood supply to the periosteum.

25. A prosthetic implant according to claim 18, wherein the first strap portion is provided on a side thereof corresponding to the bearing surface with a plurality of grooves which separate corresponding lands one from another.

26. A prosthetic implant according to claim 18, wherein the locking means comprises a plug adapted for passage through a bore made in overlapping ends of the first and second strap portions and extending substantially transversely into the patient's metacarpal bone.

27. A prosthetic implant according to claim 26, wherein the plug has a snap fit end for engagement in the bore in the patient's metacarpal bone.

28. A prosthetic implant according to claim 18, wherein the elongate flexible member is adapted for passing snugly around a surgically exposed metacarpal bone of the hand and is provided with a lateral hook-shaped member whose free end is adapted for insertion in a surgically prepared cavity in the metacarpal bone intended for receipt of a metacarpal part of a total metacarpal phalangeal joint replacement.

29. A sterilised package containing a prosthetic implant according to claim 18.

* * * * *